US006537573B2

(12) United States Patent
Johnson et al.

(10) Patent No.: US 6,537,573 B2
(45) Date of Patent: *Mar. 25, 2003

(54) COMBINATION DOSAGE FORM COMPRISING CETIRIZINE AND PSEUDOEPHEDRINE

(75) Inventors: Barbara A. Johnson, Niantic, CT (US); Richard W. Korsmeyer, Old Lyme, CT (US); Cynthia A. Oksanen, Stonington, CT (US)

(73) Assignee: Pfizer Inc, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/755,791

(22) Filed: Jan. 5, 2001

(65) Prior Publication Data

US 2002/0012700 A1 Jan. 31, 2002

Related U.S. Application Data

(62) Division of application No. 08/864,490, filed on May 28, 1997, now Pat. No. 6,171,618.
(60) Provisional application No. 60/015,865, filed on May 29, 1996.

(51) Int. Cl.[7] ............................. A61K 9/24; A61K 9/36; A61K 9/16
(52) U.S. Cl. ..................... 424/472; 424/480; 424/490
(58) Field of Search .................. 424/472, 480, 424/490, 474

(56) References Cited

U.S. PATENT DOCUMENTS

| 4,792,448 A | | 12/1988 | Ranade | 424/438 |
|---|---|---|---|---|
| 4,915,954 A | | 4/1990 | Ayer et al. | 424/473 |
| 4,996,061 A | | 2/1991 | Webb, et al. | 424/475 |
| 5,085,865 A | * | 2/1992 | Nayak | 424/472 |
| 5,395,626 A | * | 3/1995 | Kotwal et al | 424/472 |
| 5,558,879 A | * | 9/1996 | Chen et al. | 424/480 |
| 5,627,183 A | | 5/1997 | Gray | 514/255 |
| 5,654,005 A | | 8/1997 | Chen et al. | 424/480 |
| 5,807,579 A | | 9/1998 | Vilkov et al. | 424/469 |
| 6,171,618 B1 | * | 1/2001 | Johnson et al. | 424/472 |

FOREIGN PATENT DOCUMENTS

| CA | 1220137 | 4/1987 | ............ A61K/9/22 |
|---|---|---|---|
| CA | 1297026 | 3/1992 | ........... A61K/31/44 |
| CA | 1314485 | 3/1993 | ............ A61K/9/24 |
| CA | 2147606 | 5/1994 | ......... A61K/31/135 |
| CA | 2163121 | 12/1994 | ............ A61K/9/30 |
| CA | 2185893 | 9/1995 | ......... A61K/31/135 |
| CA | 2217226 | 10/1996 | ............ A61K/9/22 |
| CA | 2054752 | 12/1996 | ......... A61K/31/445 |
| EP | 0281708 | 9/1988 | ............ A61K/9/22 |
| EP | 0294993 | 12/1988 | ............ A61K/9/44 |
| EP | 0311067 | 4/1989 | ............ A61K/9/24 |
| EP | 0357369 | 3/1990 | ............ A61K/9/22 |
| EP | 0396404 | 11/1990 | ......... A61K/31/445 |
| EP | 0811374 | 12/1997 | ......... A61K/31/135 |
| WO | WO 9013295 | 11/1990 | ......... A61K/31/445 |
| WO | 9202212 | 2/1992 | ............ A61K/9/32 |
| WO | 9428880 | 12/1994 | ............ A61K/9/20 |
| WO | 9507103 | 3/1995 | .......... A61K/45/06 |

OTHER PUBLICATIONS

Database Medline US (NLM), Bethesda, MD, US Acc. Nr. 97030129, Jun. 1996 Betrand B et al.

* cited by examiner

Primary Examiner—Thurman K. Page
Assistant Examiner—Todd D Ware
(74) Attorney, Agent, or Firm—Peter C. Richardson; Gregg C. Benson; James T. Jones

(57) ABSTRACT

A dosage form containing cetirizine as an immediate release component and pseudoephedrine or a pharmaceutically acceptable salt thereof as a controlled release component. A portion of the pseudoephedrine can also be incorporated as an immediate release component. The dosage form is free of alcohols having a molecular weight lower than 100 and reactive derivatives thereof.

11 Claims, No Drawings

COMBINATION DOSAGE FORM COMPRISING CETIRIZINE AND PSEUDOEPHEDRINE

This is a divisional of application Ser. No. 08/864,490, filed May 28, 1997, now U.S. Pat. No. 6,171,618 which claims priority from co-pending Provisional Application No. 60/015,865, filed May 29, 1996.

FIELD OF THE INVENTION

This invention relates to dosage forms comprising cetirizine and pseudoephedrine, containing both a sustained release and an immediate release component.

BACKGROUND OF THE INVENTION

Cetirizine has the formula

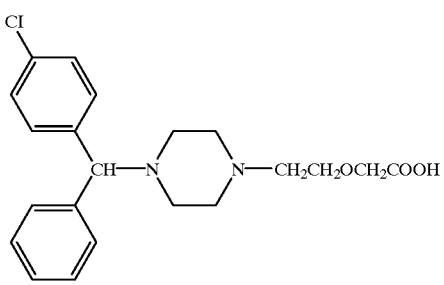

(I)

and is a member of the class of compounds termed 2-[4-(diphenylmethyl)-1-piperazinyl]acetic acids. These compounds are useful as antiallergens, spasmolytics, and antihistamines which are generally non-sedating. See U.S. Pat. No. 4,525,358 and The Merck Index, Eleventh Edition, 1989, page 310, entry 2013.

Pseudoephedrine, as well as pharmaceutically acceptable acid addition salts thereof such as the hydrochloride and sulfate salts, is a sympathomimetic drug known by those skilled in the art as a safe therapeutic agent for treating nasal congestion. It is commonly administered orally and concomitantly with an antihistamine for treatment of nasal congestion for the treatment of allergic rhinitis.

Cetirizine and pseudoephedrine can be administered together. The general schedule for administering the two drugs together involves one 10 mg cetirizine tablet per day, plus eight 30 mg immediate-release pseudoephedrine tablets divided into four doses over the course of a day. It is well known, however, that patient compliance with a multiple dose daily administration schedule can be affected by the inconvenience of having to remember to take medicine at numerous, appropriately spaced intervals. It would accordingly be useful if patients could take cetirizine plus pseudoephedrine as a unitary dosage form, such as a tablet, say oncedaily or twice-daily, to improve convenience and better ensure patient compliance.

SUMMARY OF THE INVENTION

In one aspect, this invention provides a solid dosage form comprising cetirizine and pseudoephedrine wherein at least a portion of said pseudoephedrine is contained in a core comprising said portion of pseudoephedrine, whereby release of said pseudoephedrine into an environment of use is sustained;

wherein said cetirizine is contained as an immediate-release component in said dosage form; and wherein said dosage form is substantially free of alcohols having a molecular weight lower than 100 and reactive derivatives thereof.

In a preferred embodiment, this invention provides a solid dosage form comprising cetirizine and pseudoephedrine, wherein at least a portion of said pseudoephedrine is contained in a core comprising said portion of pseudoephedrine, said core being surrounded by a permeable membrane, whereby release of said pseudoephedrine into an environment of use is sustained;

wherein said cetirizine is contained as an immediate-release component in said dosage form; and wherein said dosage form is substantially free of alcohols having a molecular weight lower than 100 and reactive derivatives thereof.

In a preferred embodiment, the dosage form is substantially free of alcohols having a molecular weight less than 250, and reactive derivatives thereof. In a more preferred embodiment, the dosage form is substantially free of alcohols having a molecular weight less than 500 and reactive derivatives thereof. In a still more preferred embodiment, the dosage form is substantially free of alcohols having a molecular weight less than 1000 and reactive derivatives thereof.

This invention further provides a process for making a solid dosage form containing cetirizine and pseudoephedrine, comprising coating a shaped sustained release core comprising pseudoephedrine with an immediate release layer comprising cetirizine and a water soluble film forming polymer, said core and said immediate-release layer being substantially free of alcohols having a molecular weight lower than 100 and reactive derivatives thereof.

In a preferred embodiment this invention provides a preferred process for making a solid dosage form containing cetirizine and pseudoephedrine, comprising the steps of coating a shaped composition comprising pseudoephedrine with a permeable membrane coating said permeable membrane with an immediate release layer comprising cetirizine and a water soluble film forming polymer, said composition, said membrane, and said layer being substantially free of alcohols having a molecular weight lower than 100 and reactive derivatives thereof.

"Cetirizinen" as employed herein is intended to include not only the free compound of formula (I) but also any pharmaceutically acceptable salt thereof. Preferred are acid addition salts, especially the dihydrochloride (referred to also herein as the "hydrochloride"). "Cetirizine" is also intended to cover individual enantiomers as well as the racemate.

"Pseudoephedrine" as employed herein is intended to be inclusive of the free base and also of any pharmaceutically acceptable acid addition salt. Preferred for use in this invention are the sulfate and hydrochloride salts.

The term "alcohols" is used generically to mean any compound having one or more hydroxyl (—OH) groups reactive toward cetirizine. The term is thus inclusive of diols and polyols as well as mono-alcohols which are reactive toward cetirizine under normal conditions of processing and storage.

A "reactive derivative" as used herein includes those materials having alcohol (—OH) groups which have been esterified and which can react with cetirizine by transesterification.

"Shaped" usually means round or roughly spherical, but can also mean any other shape that tablet cores can be made in.

The invention provides a dosage form containing both cetirizine and pseudoephedrine. The cetirizine is contained in an immediate-release component from which it starts to be delivered or released substantially immediately upon ingestion (i.e., upon swallowing). No mechanism has been incorporated into the dosage form to delay the release which would otherwise take place upon exposure to a use environment, such as the luminal fluid of the gastrointestinal (GI) tract. Generally the cetirizine should be at least 80% released from the dosage form within an hour after administration.

The pseudoephedrine, by contrast, releases in a sustained fashion, at least about 75% of the drug contained in the dosage form releasing over a period of 4 to 36 hours, preferably about 8 to about 24 hours, although the period of sustained release can be tailored to have an immediate release component, as disclosed further below. The term "about" as used above and elsewhere herein means plus or minus 10% for each of the numerical limits. The sustained release pseudoephedrine is contained in a core which can be engineered in a variety of ways and embodiments to implement sustained release. For example, the pseudoephedrine can be incorporated into a sustained release matrix that meters pseudoephedrine out over a period of 4 to 36 hours, the matrix thus constituting the core. Alternatively, the pseudoephedrine core can comprise a shaped pseudoephedrine immediate release composition and a surrounding, rate limiting membrane which imparts sustained release behavior to the core.

In the final product dosage form (i.e., the dosage form intended to be sold or administered), and during processing when making the dosage form, it is important to avoid contact of cetirizine with alcohols having a molecular weight less than 100 since such contact can result in a reaction with cetirizine, usually esterification, and thereby damage the dosage form by reacting with the active medicinal agent. Thus, the dosage form should be substantially free of such reactive components at the time the immediate-release cetirizine component is introduced into the dosage form, and thereafter. Alcohols and other reactive components can be employed during processing, so long as they are removed to reduce or eliminate their presence prior to introducing cetirizine. Not employing alcohols at all during processing, or removing them prior to introducing cetirizine into the dosage form, is what is meant by the phrase "substantially free of alcohols having a molecular weight less than . . . ". Some level of alcohols which are reactive with cetirizine can be tolerated in the final dosage form, the exact level depending on the particular alcohol. In general, to be "substantially free" of alcohol(s) the total amount of alcohol of molecular weight less than 100, whether a single alcohol or a mixture, should be less than the amount which would be required to react with 5% of the cetirizine in the dosage form, preferably less than the amount which would be required to react with 1% of the cetirizine. More preferably, it is preferred that the level of alcohol having a molecular weight less than 100, whether a single alcohol or a mixture, be less than that amount of alcohol required to react with 0.5% of the cetirizine in the dosage form, and most preferably that the dosage form be totally free of alcohols having a molecular weight less than 100.

Thus the final dosage form, in both the core and outside layer(s), must be substantially free of low molecular weight alcohols and reactive derivatives thereof. Such materials include relatively low molecular weight monohydric and polyhydric alcohols which are conventionally known and frequently, if not universally, used as solvents in the formulations arts, and compositions containing them as vehicles or carriers. Examples of such reactive alcohols include lower molecular weight alcohols such as methanol, ethanol, isopropanol, and glycerin. Because they are difficult to remove, high boiling point alcohols such as glycerin can be problematic, and it is preferred such components be avoided altogether. Many plasticizers are alcohols, and contact with cetirizine should accordingly be avoided as well if they have a low molecular weight. Many plasticizers are also esters, i.e., materials which are reactive derivatives of alcohols, and contact of cetirizine with these materials should be avoided as well since the ester groups can undergo transesterification with cetirizine and thereby damage the dosage form. Not all alcohol group-containing components are reactive toward cetirizine under normal conditions of processing and storage (temperatures less than 100° C.), however, and such components are not "alcohols" for purposes of this invention. Examples include cellulosic materials containing free hydroxyl groups, such as microcrystalline celluloses used as compressible excipients as well as cellulose ethers and esters useful as coatings in the formulations described herein.

Specific dosage forms contemplated for use in this invention include tablets, capsules, and dosage forms comprising a plurality of particles, referred to herein as a "multiparticulate dosage form", or "multiparticulate" for short. A multiparticulate can have numerous formulation applications. For example, a multiparticulate may be used as a powder for filling a capsule shell, or used per se for mixing with food, for example ice cream, to increase palatability.

The cetirizine can be incorporated into the dosage form as an "immediate release" component in a variety of ways. For example, it can be incorporated into an exterior coating for a tablet from which it releases substantially immediately upon ingestion. The coating can be all-covering, or can cover less than the surface of the dosage form, as described below. Such a coating can similarly be applied to each of the particles comprising a multiparticulate. If the dosage form is to be a capsule, the cetirizine can be contained in a single pellet inside the capsule from which it releases substantially immediately once the capsule shell dissolves. Alternatively, the cetirizine can be contained in several smaller pellets or be present as immediate release particles. In this type of capsule embodiment, the pseudoephedrine is generally present, for example, as a slow release multiparticulate, each particle comprising a central core of pseudoephedrine incorporated into a matrix or surrounded by a rate-limiting membrane.

The term "tablet" refers to the conventional macroscopic dosage form as known in the art, and as applied to this invention indicates a unitary dosage having a central core which releases pseudoephedrine in a sustained fashion, over a period of 4 to 36 hours, preferably about 8 to about 24 hours. As previously mentioned the core can be a matrix which meters out pseudoephedrine. Alternatively, the pseudoephedrine core can be formed from an immediate release, pseudoephedrine-containing composition which is surrounded by a water insoluble, permeable, rate-limiting membrane that provides for sustained release of pseudoephedrine by limiting the rate at which pseudoephedrine diffuses into the environment of use. The core is in turn coated over at least a portion of its surface with a layer comprising cetirizine and a water soluble film forming polymer that provides immediate release. The immediate release cetirizine-containing layer is preferably coated over the entire surface of the core for convenience in formulating the tablet. The immediate release layer can also, if desired, be made to cover less than the entire area of the membrane by conventional procedures known to the art. For example, if the tablet has flat surfaces, the cetirizine-containing layer can be coated exclusively onto one or more, but less than all, of the surfaces. If the tablet is spherical, the cetirizine-containing layer can be coated over less than the entire surface of the sphere. A tablet dosage form is desirable as a pre-made, readily available dosage form which can be administered in the majority of cases to patients who need and/or desire a medication containing both an antihistamine plus a decongestant.

In the case of a pseudoephedrine-containing core surrounded by a rate limiting membrane, the membrane is "permeable". Permeability can be achieved by implementing a coating which completely surrounds the core and which has a pore size that allows the passage of both water and pseudoephedrine through the membrane. In this type of membrane, water crosses the membrane into the core and dissolves the pseudoephedrine so that pseudoephedrine is released back across the membrane into the GI tract at a desired rate, i.e. a rate which is reasonably constant until substantially all of the pseudoephedrine has been released over a period of 4 to 36 hours. This type of membrane is disclosed and described, for example, in EP-A-0 357 369, herein incorporated by reference in its entirety. Alternatively, the membrane can be permeable to water only, but have one or more openings such as a round hole or other shape opening, shape not being critical. The opening can be physically implemented, for example by drilling, somewhere on the surface to allow the release of pseudoephedrine. This type of dosage is known to the art and described in numerous U.S. Pat. Nos., including 4,915,954; 4,915,953; 4,915,952; 4,847,093; and 4,810,502; each of which is herein incorporated by reference in its entirety.

The term "multiparticulate dosage form" or "multiparticulate" is intended to embrace a dosage form comprising a multiplicity of particles whose totality represents the intended therapeutically useful dose of cetirizine plus pseudoephedrine. The particles generally are of a diameter from about 50 microns to about 0.3 cm, with a preferred range of 100 μm to 1 mm. Each individual particle is in essence a mini-tablet, and each comprises a central sustained release core of pseudoephedrine, with sustained release being implemented as described above. Each can also be coated, fully or partially, with an immediate release layer comprising cetirizine plus a water soluble film forming polymer.

In an alternative embodiment, a pseudoephedrine-containing matrix or membrane-coated multiparticulate, with no cetirizine-containing immediate-release coating, can be used to partially fill a capsule and one or more pellets of immediate-release cetirizine can be added as part of the capsule fill. A multiparticulate dosage form is desirable since it allows customizing or tailoring according to the weight of the patient by simply scaling the number of particles in the dosage form. Thus, for example, a weight of multiparticulate adapted for a particular patient or group of patients who may need more or less of the medication than that supplied in a pre-made tablet, can be used as fill for a capsule. Capsules adapted for larger or smaller patients can be tailored by simply adjusting, up or down as appropriate, the fill weight of multiparticulate.

If a multiparticulate is membrane-coated the individual particles are typically formed so that the membrane completely surrounds the central pseudoephedrine core and, in the use environment, is permeable to both water and pseudoepedrine.

In one dosage form embodiment of the invention, all of the cetirizine is incorporated into a separate (i.e, from the sustained release core) immediate-release coating that surrounds the pseudoephedrine core of the dosage form, and all of the pseudoephedrine is incorporated into the core. This embodiment can take the form of a macroscopic tablet, or the form of a multiparticulate for use as capsule fill.

In an alternative embodiment, all of the cetirizine and part of the pseudoephedrine is incorporated into the separate layer immediate release coating and the remainder of the pseudoephedrine is incorporated into the sustained release core. This alternative embodiment provides some of the pseudoephedrine for immediate release along with the immediate-release cetirizine also in the coating.

The amount of cetirizine administered can vary with the size of the patient, as discussed above, but will generally be in the range of about 5 to about 20 mg/day. The amount of pseudoephedrine administered will generally vary from about 60 to about 240 mg/day. Up to about 25% of the pseudoephedrine, corresponding to 15–60 mg/day, can be incorporated into the immediate release cetirizine-containing layer, thereby providing that amount for immediate release together with the cetirizine. It is preferred to incorporate all of the pseudoephedrine into the core, however.

The fact that alcohols and derivatives thereof such as esters are deleterious to formulations containing cetirizine is surprising in view of the fact that esters, for example glycerol esters, of cetirizine are difficult to make by conventional direct esterification methods. In view of the difficulty associated with direct esterification, it is surprising that cetirizine reactivity towards alcohols is such that extensive ester formation was observed when using processes to make dry solid formulations, such as tablets, in which cetirizine was exposed to glycerin or other alcohols in one or more steps.

DETAILED DISCUSSION

Any dosage form useful in this invention can be tested to determine if a particular alcohol is potentially deleterious by the following procedure. The dosage form can be stored at 50° C. for twelve weeks in a closed container (including the commercial container, if closable) and then dissolved in water. Following filtration, an aqueous sample can be injected in a liquid chromatograph and analyzed for the presence of cetirizine esters by reverse phase high performance liquid chromatography (HPLC) using UV detection at 231 nm. For the reverse phase system, a column having a C-18 hydrocarbon stationary phase, of the type designated as an Ultrasphere (registered trademark of Beckman Instruments, Inc.) C-18 ODS column, can be employed using an isocratic mobile phase consisting of 60% water having a pH of 2.5 (pH adjusted by adding potassium dihydrogen phosphate) and 40% acetonitrile. Flow rate is typically 1 mL/minute. Cetirizine esters usually elute after cetirizine. Identification can be by comparison of an unknown peak with a known standard which elutes at the same retention time. Confirmation can be by mass spectrometry.

Sustained release cores are made from a matrix material in which pseudoephedrine is embedded or dispersed and which acts to retard the release of pseudoephedrine into the environment of use, the GI tract. When pseudoephedrine is embedded in a matrix of this sort, release of the drug takes place principally from the surface of the matrix. Thus the drug is released from the surface of the matrix after it diffuses through or when the surface of the matrix erodes, exposing the drug. In some matrices, both mechanisms can operate simultaneously. These types of systems are well known to the art and are discussed extensively, for example, in PCT/IB95/00264, published as WO 95/30422, herein incorporated by reference in its entirety.

A preferred embodiment of a matrix core has the form of a hydrophilic matrix, i.e., a core containing pseudoephedrine and, as matrix, an amount of hydrophilic polymer sufficient to provide a useful degree of control over the pseudoephedrine dissolution. Hydrophilic polymers useful for forming the matrix include hydroxypropyl methylcellulose (HPMC), hydroxypropyl cellulose (HPC), poly(ethylene oxide), poly (vinyl alcohol), xanthan gum, carbomer, carrageenan, and zooglan. A preferred material is HPMC. Other similar hydrophilic polymers may also be employed. In use, the hydrophilic material is swollen by, and eventually dissolves in, water. The pseudoephedrine is released both by diffusion from the matrix and by erosion of the matrix. The pseudoephedrine dissolution rate from a hydrophilic matrix core may be controlled by the amount and molecular weight of hydrophilic polymer employed. In general, using a greater amount of the hydrophilic polymer decreases the dissolution rate, as does using a higher molecular weight polymer. Using a lower molecular weight polymer increases the dissolution rate. The dissolution rate may also be controlled by the use of water soluble additives such as sugars, salts, or soluble polymers. Examples of these additives are sugars such as lactose, sucrose, or mannitol, salts such as NaCl, KCl, NaHCO$_3$, and water soluble polymers such as poly(N-vinyl-2-pyrrolidinone) or polyvinylpyrrolidone, low molecular weight HPC or HMPC or methylcellulose. In general, increasing the fraction of soluble material in the formulation increases the release rate. A hydrophilic matrix core typically comprises about 20 to 90% by weight of pseudoephedrine and about 80 to 10% by weight of polymer.

A pseudoephedrine hydrogel matrix core can be coated with an immediate release coating comprising cetirizine and a water soluble film forming polymer.

A preferred matrix composition for use as a core comprises, by weight, about 50% to about 80% pseudoephedrine, about 15% to about 35% HPMC, 0% to about 35% lactose, 0% to about 15% PVP, 0% to about 20% microcrystalline cellulose, and about 0.25% to about 2% magnesium stearate.

The matrix systems as a class often exhibit non-constant release of the drug from the matrix. This result may be a consequence of the diffusive mechanism of drug release, and modifications to the geometry of the dosage form can be used to advantage to make the release rate of the drug more constant as detailed below.

In a particular embodiment, a pseudoephedrine matrix core can be coated with an impermeable coating, and an orifice (for example, a circular hole or a rectangular opening) can be provided by which the content of the tablet is exposed to the aqueous GI tract. This embodiment is along the lines of those presented in U.S. Pat. No. 4,792,448 to Ranade, herein incorporated by reference. The opening is typically of a size such that the area of the exposed underlying pseudoephedrine composition constitutes less than about 40% of the surface area of the device, preferably less than about 15%. The entire core can be coated with an immediate release layer comprising cetirizine and a water soluble film forming polymer.

In a further particular embodiment, a pseudoephedrine hydrogel matrix core can be coated with an impermeable material and an opening for drug transport produced by drilling a hole through the coating. The hole may be through the coating only, or may extend as a passageway into the core. The entire core can be coated with an immediate release layer comprising cetirizine and a water soluble film forming polymer.

In a further particular embodiment, a pseudoephedrine hydrophilic matrix core can be coated with an impermeable material and a passageway for drug transport produced by drilling a passageway through the entire tablet. The entire core can be coated with an immediate release layer comprising cetirizine and a water soluble film forming polymer.

In a further particular embodiment, a pseudoephedrine hydrogel matrix core can be coated with an impermeable material and one or more passageways for drug transport produced by removing one or more strips from the impermeable coating or by cutting one or more slits through the coating, preferably on the radial surface or land of the tablet. The entire core can be coated with an immediate release layer comprising cetirizine and a water soluble film forming polymer.

In a further particular embodiment, a pseudoephedrine hydrogel matrix core can be shaped in the form of a cone and completely coated with an impermeable material. A passageway for drug transport can then be produced by cutting off the tip of the cone and the entire cone can be coated with an immediate release layer comprising cetirizine and a water soluble film forming polymer.

In a further particular embodiment, a pseudoephedrine hydrogel matrix core can be shaped in the form of a hemisphere, completely coated with an impermeable material, and a passageway for drug transport produced by drilling a hole in the center of the flat face of the hemisphere. The entire core can be coated with an immediate release layer comprising cetirizine and a water soluble film forming polymer.

In a further particular embodiment, a pseudoephedrine hydrogel matrix core can be shaped in the form of a half-cylinder and completely coated with an impermeable material. A passageway for drug transport can be produced by cutting a slit through or removing a strip from the impermeable coating along the axis of the half-cylinder or along the centerline of the flat face of the half-cylinder. The entire core can be coated with an immediate release layer comprising cetirizine and a water insoluble film forming polymer.

Those skilled in the art will appreciate that the geometric modifications to the embodiments described above can be equivalently produced by more than one method. For example, cutting or drilling to make a passageway for drug transport can be achieved by other operations such as by a technique which produces the desired partial coating directly.

The term "impermeable material" means a material having sufficient thickness and impermeability to pseudoephedrine such that no significant transport of pseudoephedrine can take place through the material during the time scale of the intended drug release (i.e., 4–36 hours). Such a coating can be obtained by selecting a coating material with a sufficiently low diffusion coefficient for pseudoephedrine and applying it to sufficient thickness. Materials for forming the impermeable coating of these embodiments include substantially all materials in which the diffusion coefficient of pseudoephedrine is less than about $10^{-7}$ cm$^2$/s. It is noted that the preceding diffusion coefficient can be amply sufficient for a matrix device, as discussed above. In a device of the type now under discussion which has been provided with a macroscopic opening, however, a material with this diffusion coefficient, and almost any membrane material that is not a liquid, looks to the contained pseudoephedrine, by contrast, as though it is impermeable because the majority of transport is through the opening. Preferred coating materials include insoluble film forming polymers and waxes. Especially preferred are thermoplastic polymers, such as poly (ethylene-co-vinyl acetate), poly(vinyl chloride), ethylcellulose, and cellulose acetate. These materials exhibit the desired low permeation rate toward pseudoephedrine when applied as coatings of thicknesses greater than about 100 µm.

When making cores which comprise an immediate release pseudoephedrine composition surrounded by a rate limiting membrane, the types of membranes which can be employed are widely known in the art, for example from the patents and publications previously mentioned including EP 0 357 369, U.S. Pat Nos. 4,847,093, and 4,915,953. The membranes can be fabricated from water insoluble film forming polymers, for example from olefin and vinyl type polymers, organosilicon polymers, polysulfones, polyamides, polyurethanes, cellulose esters, cellulose ethers and the like. The polymers can be condensation polymers or addition polymers. Specific non-cellulosic polymers include poly (methylmethacrylate), poly(butylmethacrylate), polyethylene, ethylene vinylacetate copolymer, poly (dimethylsiloxane), polypropylene, polyvinyl chloride, polyvinyl alcohol, ethylene vinylalcohol, and the like.

Cellulosic materials such as cellulose esters and ethers are preferred for use in making membranes to surround tablet cores. Examples of cellulose esters and ethers, include the mono-, di- and triacyl esters wherein the acyl group consists of two to four carbon atoms and lower alkyl ethers of cellulose wherein the alkyl group is one to four carbon atoms. The cellulose esters can also be mixed esters, such as cellulose acetate butyrate, or a blend of cellulose esters. The same variations can be found in ethers of cellulose and include blends of cellulose esters and cellulose ethers. Other cellulose derivatives which can be used for making membranes useful in the present invention include those materials which are associated with reverse osmosis membranes, and include cellulose nitrate, acetaldehyde dimethyl cellulose, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate p-toluene sulfonate, cellulose cyanoacetates, cellulose acetate trimellitate and cellulose methacrylates.

Cellulose esters can be formed by the acylation of cellulose with the corresponding acyl anhydride or acyl halide. Several of the common cellulose esters are available commercially. Cellulose acetate 394-60, 398-10 and 400-25, having acetyl contents of 39.4, 39.8 and 40%, respectively, are readily available from Eastman Chemical Co., Kingsport, Tenn.

Whether in the form of a tablet or a multiparticulate, the type of tablet core now discussed constitutes a membrane-moderated or reservoir system. In this type of sustained release system a reservoir of pseudoephedrine is surrounded by a rate-limiting membrane which allows passage of pseudoephedrine and water. The pseudoephedrine traverses the membrane by mass transport mechanisms well known in the art, including but not limited to dissolution in the membrane followed by diffusion across the membrane. As previously stated for this invention, these individual reservoir system dosage forms may be large, as in the case of a tablet containing a single large reservoir, or multiparticulate, as in the case of a capsule containing a plurality of reservoir particles, each individually coated with a membrane. The coating can be non-porous, yet permeable to pseudoephedrine (for example pseudoephedrine may diffuse directly through the membrane), or it may be porous. The particular mechanism of transport which operates to achieve sustained release is not believed to be critical.

Tablets having membrane-moderated cores can also be made as osmotic delivery systems, that is, systems such as those previously discussed in which rate-limiting membrane surrounding the pseudoephedrine core is impermeable or poorly permeable to pseudoephedrine but easily permeable to water. Water can then diffuse across the membrane and dissolve the pseudoephedrine in the core which then passes out of the tablet through one or more holes which have been drilled through or otherwise implemented through the surface of the tablet so that the hole exposes the interior of the pseudoephedrine core. The size and shape of the hole is not critical and is usually on the order of 0.05 mm to 2 mm. The term "hole" is intended to cover any exit passageway regardless of what it's termed (e.g., hole, orifice, bore, slit and so forth).

Water insoluble sustained release coatings as known in the art may be employed to fabricate the membrane which surrounds the core, especially polymer coatings, such as any of those water in soluble coatings mentioned above. Preferred materials are cellulosic materials, as previously disclosed. Particularly preferred materials include ethyl cellulose, cellulose acetate and cellulose acetate butyrate. The polymer may be applied as a solution in an organic solvent or as an aqueous dispersion or latex. The coating operation may be conducted in standard equipment such as a fluid bed coater, a Wurster coater, or a rotating perforated pan. If desired, the permeability of the membrane may be adjusted by blending of two or more materials.

A particularly useful process for tailoring the porosity of the coating comprises adding a pre-determined amount of a finely-divided water soluble material, such as sugars, salts or water soluble polymers to a solution or dispersion (e.g., an aqueous latex) of the membrane-forming polymer to be used. Additional useful pore formers include dimethyl sulfone, and nicotinamide. When the dosage form is ingested into the aqueous medium of the GI tract, these water soluble membrane additives are leached out of the membrane, leaving pores which facilitate release of the drug. The membrane coating can also be modified by the addition of plasticizer, as known in the art. These types of procedures are fully disclosed in U.S. Pat. Nos. 4,851,228, 4,687,660, and 3,538,214, all of which are herein incorporated by reference. Although alcohols are also known in the art to be useful as pore formers, including sorbitol, pentaerythritol, mannitol, and other aromatic and aliphatic mono-ols and polyols, including diols and triols, these types of alcohols as pore formers should be avoided in this process since they tend to react with cetirizine by esterification.

Pore size in the membrane is not believed to be particularly critical; rather the overall permeability of the coating is believed to be more important. The optimum pore size depends on the size of the individual core. Generally, pore size is less than 50 µm and total pore area is less than 1% of the total membrane surface area. Optimum membrane thickness also varies depending on the size of the core, i.e., on whether the core is unitary and macroscopic (e.g, for use in a unitary tablet) or multiparticulate. For unitary macroscopic cores the membrane thickness is generally 100–700 μm in thickness, with optimal thickness in most cases being 200–500 μm. For multiparticulates membrane thickness generally varies from 5 to 75 μm.

The pore size of a membrane and its thickness can be ascertained by measuring under an electron microscope. Both membrane thickness and porosity can be modified to tailor a particular device to achieve desired release characteristics.

A preferred membrane is an asymmetric membrane of the type described in EP 0 357 369. As disclosed therein, an asymmetric membrane is comprised of two regions or membrane layers. One layer is a relatively thick and porous sub-structure. This substructure supports the other portion of the membrane, a very dense, thin skin. The membrane can be made of water insoluble film forming cellulose derivatives such as the cellulose esters and ethers mentioned above. Mixed esters and ethers can be employed. Many other materials, including any of those disclosed in EP 0 357 369 can also be employed. The formulation used to make the membrane should comprise at least about 60% to 90% by weight of a water insoluble film forming polymer and, correspondingly, about 40% to 10% of a pore forming reagent such as any of those previously mentioned. For optimum results, the membrane formulation should contain from 65 to 75%, especially about 68%, by weight of a water insoluble film forming polymer with the remainder being a pore-forming reagent. A particularly useful process for applying a membrane coating comprises dissolving the coating polymer in a mixture of solvents chosen such that as the coating dries, a phase inversion takes place in the applied coating solution, resulting in a membrane with a porous structure.

In the present invention, if the rate-limiting membrane is to be an asymmetric membrane of the type described in EP 0 357 369, it is possible to pre-form the pores (as opposed to forming pores in-situ in the GI tract) by employing one or more, usually volatile, alcohols as pore-forming ingredients, but it is important that all alcohol be removed prior to applying the immediate-release layer which contains cetirizine. Thus if one or a mixture of low molecular weight alcohols is used as a pore former when making membrane-surrounded cores, the alcohol(s) should be removed after pore formation has been completed. Removal can be effected conventionally, for example by placing the cores in a forced air oven, vacuum oven, or fluidized bed for several hours, typically overnight. The alcohols employed should also be low boiling point, volatile liquids at room temperature such as methanol and ethanol. Higher boiling point alcohols which are liquid at room temperature, such as glycerol, butanol and higher mono-alcohols, and diols such as low molecular weight glycols like ethylene glycol and propylene glycol, are problematic and should be avoided altogether.

A tablet core according to the invention comprises about 60 to about 360 mg of pseudoephedrine, about 70 to about 425 mg of compressible excipients, about 2 to about 17 mg of binder, and about 0.5 to about 4 mg of lubricant. A preferred dosage form contains 240 mg of pseudoephedrine (or 120 mg if the dose is to be divided) as the hydrochloride and an amount of compressible excipient, binder, and lubricant within the ranges set above. Generally, the greater the amount of pseudoephedrine hydrochloride used in the core, the greater should be the corresponding amount of compressible excipient that is used.

The above referenced proportions and amounts are advantageous because they provide for compressible tablet cores having good mechanical properties, including ruggedness, and low wastage. Using amounts outside the above limits generally increases the likelihood of formulation and/or scale-up difficulties, including low tablet hardness, friability, and capping.

The term "compressible excipients" refers to those materials generally known to the art for use in formulations for improving flow and compression properties of a drug formulation. Preferred are materials such as microcrystalline celluloses sold as Avicels (registered trademark of FMC Corporation, Philadelphia, Pa.).

Binders are materials which generally function to hold drug and other powder ingredients together in a granulation, and conventionally known binders can also be employed in this invention. Suitable binders include water soluble polymers such as hydroxypropyl cellulose (HPC), poly(N-vinyl-2-pyrrolidinone) (PVP), and hydroxypropyl methylcellulose (HPMC). Advantageously, it is possible to purchase grades of microcrystalline cellulose which are preformulated to contain binders such as HPMC.

As lubricant, magnesium stearate is preferred, although other lubricants such as stearic acid and sodium lauryl sulfate can also be employed.

If the immediate-release cetirizine component is implemented as a coating over the rate-limiting membrane, the coating can contain about 40 to about 85% by weight of cetirizine based on the weight of the coating, with the remainder (15 to 60 weight %) being a water soluble film forming polymer such as hydroxypropyl methylcellulose (HPMC) or a blend of hydroxypropyl cellulose and hydroxypropyl methylcellulose, which can be made or purchased under the registered trademark OPADRY, from Colorcon. The water soluble film forming ingredient can also be a sugar. The coating can optionally contain other ingredients such as titanium dioxide or other suitable non-hydroxyl group containing pigment. For a (macroscopic) tablet, this coating will typically comprise from 2.5 to 20 mg of cetirizine and 4 to 50 mg of film forming polymer.

In a preferred wet granulation process for making tablets, tablet cores are first formed by blending pseudoephedrine as the hydrochloride salt with microcrystalline cellulose (e,g., Avicel® PH101) and a binder (e.g., Klucel® EXF, registered trademark of Aqualon Company) in a V-blender or a P/K processor (Patterson-Kelley). The resulting blend is then granulated with water (approximately 9–13% by weight) to make a damp mass and dried to a final moisture content of less than 1% by weight as determined from a moisture balance. The granules are then milled and blended with additional microcrystalline cellulose such as Avicel® PH 200. Lubricant can then be added and the entire mass blended in a V-blender, and non-membrane coated cores then formed by compressing the resulting blend on a tablet press.

The membrane coating solution can be formed by mixing ethyl cellulose or other suitable membrane-forming material plus a pore-forming component (e.g., polyethylene glycol having an average molecular weight of over 3000 such as PEG 3350 sold by Union Carbide Corporation under the registered trademark CARBOWAX) in a mixture of acetone and water solvent. The mixture is stirred until a solution is formed.

Tablet cores can then be added to a coating pan, the membrane forming solution sprayed on, and the coated cores dried in a tray dryer.

A solution of water soluble film forming agent (Opadry®) and cetirizine in water can then be sprayed onto the dried membrane-coated cores to apply the cetirizine coating. At this point the tablets are ready for therapeutic use. If desired, however, an additional outermost taste masking layer can be added to the tablet or to the multiparticulate. Such layer can be added in a facile manner by simply coating an additional amount of film forming polymer as an all-covering layer over the cetirizine-containing layer. If desired opacifiers such as titanium dioxide can be added to the outermost coating.

Multiparticulates can be made per the description given above for tablets, wherein each multiparticulate is in essence a mini-tablet matrix core or a core surrounded by a membrane. A preferred process for manufacturing multiparticulate cores is the extrusion/spheronization process. For this process, pseudoephedrine is wet-massed with a binder, extruded through a perforated plate or die, and placed on a rotating disk. The extrudate ideally breaks into pieces which are rounded into spheres, spheroids, or rounded rods on the rotating plate. An example of this type of process and a composition involves using water to wet granulate a blend comprising, as a matrix, about 10 to 75% of microcrystalline cellulose blended with, correspondingly, about 90 to 25% pseudoephedrine as the hydrochloride salt.

A further preferred process for manufacturing matrix multiparticulates is the preparation of wax granules. In this process, a desired amount of pseudoephedrine is stirred with liquid wax to form a homogeneous mixture, cooled and then forced through a screen to form granules. Preferred matrix materials are waxy substances. Especially preferred are hydrogenated castor oil and carnauba wax and stearyl alcohol.

A further preferred process for manufacturing matrix multiparticulates involves using an organic solvent to aid mixing of the pseudoephedrine with the matrix material. This technique can be used when it is desired to utilize a matrix material with an unsuitably high melting point that, if the material were employed in a molten state, would cause decomposition of the drug or of the matrix material, or would result in an unacceptable melt viscosity, thereby preventing mixing of pseudoephedrine with the matrix material. Pseudoephedrine and matrix material may be combined with a modest amount of solvent to form a paste, and then forced through a screen to form granules from which the solvent is then removed. Alternatively, pseudoephedrine and matrix material may be combined with enough solvent to completely dissolve the matrix material, and the resulting solution which may contain solid drug particles spray dried to form the particulate dosage form. This technique is preferred when the matrix material is a high molecular weight synthetic polymer such as a cellulose ether or cellulose ester. Solvents typically employed for the process include acetone, ethanol, isopropanol, ethyl acetate, and mixtures of two or more.

Dosage forms according to the invention can be tested to measure the rate of release both of cetirizine and of pseudoephedrine by the following procedure which employs a USP Apparatus 2 as decribed in USP Chapter <711>. The apparatus is implemented to run at a paddle speed of 50 rpm, with one liter of distilled water at 37° C. The dosage form is added to the apparatus and the cetirizine is monitored by HPLC with UV detection to ascertain when the cetirizine concentration reaches a steady value. Typical times at which the cetirizine concentration is monitored are at 15 minutes, 30 minutes, 45 minutes, and 1 hour after addition, although different or additional times can also be used. The point at which the immediate-release cetirizine concentration reaches a steady value is the time at which release is on the order of 80% complete, typically less than one hour. The pseudoephedrine concentration is similarly monitored at two hour intervals, starting at the first two hour mark after adding the dosage form to the USP Apparatus 2, until the concentration has leveled out.

The HPLC system used to monitor the USP aqueous medium can be the same reverse phase system for both cetirizine and pseudoephedrine. The column is typically a C-18 CN column, of the type available under the registered trademark ZORBAX from Mac-Mod. The mobile phase is maintained at 30° C. and can be an isocratic combination of 1:1 (v/v) water/methanol with the pH adjusted to 6.5 by adding sodium dihydrogen phosphate and sodium hydroxide, as appropriate, and made 5 mM in 1-octanesulfonic acid sodium salt. Detection can be effected for both cetirizine and pseudoephedrine with a UV detector at 214 nm. Typical retention times are 3–4 minutes for pseudoephedrine and 8–9 minutes for cetirizine, thus assuring reasonably good separation.

The invention is further disclosed and detailed in the following examples, which are not to be taken as limiting:

EXAMPLE 1

This example illustrates that the use of common alcoholic components can be problematic.

A pseudoephedrine tablet core of the composition given below was made by the following procedure. A wet granulation of ingredients 1–5 was prepared with a 50/50 solution of isopropyl alcohol and ethanol, ingredients 6–7. Sufficient solvent addition and mixing of the granulation resulted in a doughy mass that was subsequently crumbled and dried in an oven. The dried granulation was properly sized by comminution. An acceptably sized form of sodium chloride was added to make up 5.6% of the said granulation. To this, 0.5% of magnesium stearate was added to serve as a tabletting aid. The granulation was compressed into tablet cores containing approximately 180 mg of pseudoephedrine using 13/32" standard round concave tooling on a conventional rotary tablet press.

TABLET CORE

| Component | Grade | % w/w of finished blend and tablet | Weight (mg/tablet) |
| --- | --- | --- | --- |
| 1. Pseudoephedrine HCl | USP | 40.00 | 180.00 |
| 2. Lactose, Anhydrous | NF | 15.37 | 69.15 |
| 3. Calcium Phosphate Dibasic, Anhydrous | USP | 24.93 | 112.20 |
| 4. Ethylcellulose, Standard 100 Premium | NF | 9.07 | 40.80 |
| 5. Povidone (Plasdone C-15) | USP | 4.53 | 20.40 |
| 6. Isopropyl Alcohol | USP | | (45.00)* |
| 7. Ethanol, 95% | USP | | (45.00)* |
| 8. Sodium Chloride | USP | 5.60 | 25.20 |
| 9. Magnesium Stearate | NF | 0.50 | 2.25 |
| Total | | 100.00 | 450.00 |

*() denotes a volatile component, not present in the final dosage form.

The membrane coating described in the table below was applied to the tablet cores in a perforated tablet coating pan (Hi-Coater, HCT-30, Vector Corp.). A tablet core batch of about 825 grams was coated by spraying the membrane solution at about 27 g/min while maintaining an outlet temperature of about 19° C. After a 30% (by weight) membrane was applied, the coated cores were dried for approximately 12–16 hours at 50° C. on trays in a forced air oven.

MEMBRANE COATING

| Component | Grade | % w/w of coating solution | Weight (mg/tablet) |
|---|---|---|---|
| 1. Pseudoephedrine HCl 180 mg Tablet Core | | | 450.00 |
| 2. Ethylcellulose, Standard 10 Premium | NF | 4.2 | 81.00 |
| 3. Cellulose Acetate | NF | 0.5 | 9.00 |
| 4. Glycerin 99.5% (Glycerol) | USP | 2.3 | 45.00 |
| 5. Purified Water | USP | 2.8 | (54.00)* |
| 6. Isopropyl Alcohol | USP | 12.4 | (239.14)* |
| 7. Ethanol, 95% | USP | 22.8 | (439.71)* |
| 8. Acetone | NF | 55.0 | (1060.71)* |
| Total | | 100.00 | 585.00 |

*() denotes a volatile component, not present in the final dosage form.

The dried membrane-coated cores were subsequently coated with the cetirizine HCl-containing coating that also included a 60 mg dose of pseudoephedrine hydrochloride shown in the following table. The drug layer was overcoated onto about 900 grams of membrane coated cores in a perforated tablet coating pan (Hi-Coater, HCT-30, Vector Corp.). The drug solution was sprayed at about 9 g/min while maintaining an outlet temperature of 35–40° C. Enough drug layer was applied so that the tablet cores were overcoated with about 60 mg of pseudoephedrine hydrochloride and about 10 mg of cetirizine hydrochloride.

CETIRIZINE/PSEUDOEPHEDRINE COATING

| Component | Grade | % w/w of coating soln | Weight (mg/tablet) |
|---|---|---|---|
| 1. Pseudoephedrine HCl 180 AM Coated Tablet | Pharm | | 585.00 |
| 2. Pseudoephedrine HCl | USP | 6.5 | 60.00 |
| 3. Cetirizine HCL[] | Pharm | 1.1 | 10.00 |
| 4. Opadry, Clear (YS-1-7006) | Pharm | 6.0 | 55.50 |
| 5. Purified Water | USP | 86.4 | (797.30)* |
| Total | | 100.00 | 710.50 |

*() denotes a volatile component, not present in the final dosage form.

To these tablets a further taste masking layer was applied by spraying a 5% aqueous solution of Opadry, clear (YS-1-7006) increasing the individual tablet weight by about 20 mg. The solution was sprayed at 6 g/min while maintaining an exhaust temperature of 35° C.

TASTE MASK COATING

| Component | Grade | % w/w of coating soln | Weight (mg/tablet) |
|---|---|---|---|
| 1. Cetirizine HCl/Pseudoephedrine HCl (10/240 mg) Tablet | Pharm | | 710.50 |
| 2. Opadry, Clear (YS-5-1-7006) | Pharm | 5.0 | 19.50 |
| 3. Purified Water | USP | 95.0 | (370.50)* |
| Total | | 100.00 | 730.00 |

*() denotes a volatile component, not present in the final dosage form.

These overcoated tablets were subjected to the following storage conditions as part of an accelerated stability study (note: "RH" means relative humidity): 50° C./20% RH, 40° C./75% RH and 5° C. After three weeks, the following degradation of cetirizine to the cetirizine ester of glycerol (CEG) was determined.

| Storage Conditions | % CEG as determined relative to the cetirizine peak |
|---|---|
| 50° C./20% RH | 57% |
| 40° C./75% RH | 43% |
| 5° C. | 17% |

EXAMPLE 2

This example demonstrates a preferred method and composition.

A pseudoephedrine tablet core of the composition given below was prepared by the following procedure. First, 155 kg of granulation was prepared by combining components 1, 2, and 3 (in the proportions shown) in a 10 ft³ twin shell blender equipped for wet granulation ("P-K Processor", Patterson-Kelly Corp., East Stroudsburg, Pa., USA). The blended components were granulated by the addition of water (component 4). Upon completion of water addition, mixing was continued for 3 minutes, and then the wet mass was dried in-situ by application of vacuum at 60° C. with agitation. When the water content of the granulation had reached a level of less than 1% (determined by loss-on-drying measurement), the dried granulation was passed through a mill and divided into two equal portions for subsequent processing. One portion of the dried granulation was then combined with microcrystalline cellulose (component 5) in the P-K Processor, blended for 15 minutes, milled, blended again for 15 minutes and then blended with magnesium stearate (component 6) for 5 minutes to yield the final blend, suitable for tabletting on a high speed press. The blend was tabletted on a Manesty Mark IIa tablet press using $7/16$" standard round concave tooling to yield a batch of tablet cores of nominal weight 535 mg each.

TABLET CORE

| Component | Weight (mg/tablet) |
|---|---|
| 1. Pseudoephedrine HCl | 240.00 |
| 2. Microcrystalline cellulose, NF (Avicel PH 101) | 67.48 |
| 3. Hydroxypropyl cellulose, NF (Klucel EXF) | 10.82 |
| 4. Purified Water, USP | *(31.80) |
| 5. Microcrystalline cellulose, NF (Avicel PH 200) | 213.98 |
| 6. Magnesium Stearate, NF | 2.67 |
| | 534.95 mg |

*Note: water is used in process, but removed

The tablet cores prepared above were then coated with the solution shown below in a perforated pan coater ("HiCoater, HCT-60", Vector Corp.). A 10 kg batch of cores was coated by spraying the coating solution at approximately 175 g/min with an outlet air temperature maintained at 35° C. until the requisite coating weight was obtained. The cores were subsequently dried in an oven at 50° C. for 16 hours.

| MEMBRANE COATING SOLUTION | |
| --- | --- |
| Component | Weight (mg/tablet) |
| Ethylcellulose Std. 100 Prem. | 59.84 |
| Polyethylene Glycol 3350 | 31.11 |
| Purified Water | (70.03) |
| Acetone | (748.53) |
| | 90.94 mg |

The cores prepared above were further coated with cetirizine by spraying them with the solution shown below in the HiCoater using two spray guns at a solution application rate of 20 g/minute per gun and an outlet air temperature of 45° C. Application of the correct amount of drug to each tablet was verified by measuring the weight gain of a sample of 100 tablets and confirmed by UV analysis. The cetirizine-coated tablets were further coated with the taste-mask coating by spraying them with the taste-mask coating solution (also shown below) at an application rate of 60 g/minute using one spray gun and an outlet air temperature of 45° C. to yield the final product.

| CETIRIZINE COATING SOLUTION | |
| --- | --- |
| Component | Weight (mg/tablet) |
| Cetirizine HCl | 10.00 |
| Opadry, Clear (YS-5-19010) | 19.30 |
| Purified Water | (470.70) |
| | 29.3 mg |

| TASTE MASK COATING | |
| --- | --- |
| Component | Weight (mg/tablet) |
| Opadry, White (YS-5-18011) | 19.70 |
| Purified Water | (177.30) |
| | 20.20 mg |

EXAMPLE 3

This example demonstrates a method and composition for making a tablet within the scope of the invention.

| TABLET CORE | |
| --- | --- |
| Component | Weight (mg/tablet) |
| Pseudoephedrine HCl | 240.00 |
| Microcrystalline cellulose, NF (Avicel PH 101) | 67.50 |
| Microcrystalline cellulose, NF (Avicel PH 200) | 214.00 |
| Hydroxypropyl cellulose, NF | 10.82 |
| Purified Water, USP | (31.80) |
| Magnesium Stearate, NF | 2.67 |
| | 534.99 mg |

Membrane Coating Solution

The following membrane coating was used to coat tablet cores with an asymmetric membrane as defined and disclosed in EP 0 357 369.

| Component | Weight (mg/tablet) |
| --- | --- |
| Ethylcellulose Std. 100 Prem. | 74.90 |
| Polyethylene Glycol 3350 | 32.11 |
| Purified Water | (84.53) |
| Acetone | (878.47) |
| | 107.00 mg |
| CETIRIZINE COATING | |
| Cetirizine HCl | 10.00 |
| Opadry Clear (YS-19010) | 19.30 |
| Purified Water | (303.70) |
| | 29.3 mg |
| TASTE MASK COATING | |
| Opadry, White (YS-5-18011) | 19.70 |
| Purified Water | (181.80) |
| | 20.20 mg |

Method of Manufacture

Pseudoephedrine HCl, microcrystalline cellulose and hydroxypropyl cellulose were blended in a 2 cubic foot P-K processor for 15 minutes, milled through a Fitz mill (using size 2AA plate and knives forward) and blended for 15 minutes. The blend was wet granulated in the P-K processor with 9% water by weight. The granulation was dried in the P-K processor using a jacket temperature of 60° C., to a final water content of less than 1% by loss on drying. The dried granulation was milled through a Fitz mill (using size 2A plate and knives forward), blended for 10 minutes in a 5 cubic foot twin shell blender. Microcrystalline cellulose was added and blended for 15 minutes. Magnesium stearate was added and blended for 5 minutes. The granulation was compressed on a Kilian LX21 tablet press using 7/16" SRC tooling at a tablet hardness of 10 kp. The asymmetric membrane coating was applied to the tablets in an HCT-60 coater using a spray rate of 140 g/min, then dried for 16 hours in a Stokes forced hot air dryer. The asymmetric membrane coated tablets were coated with cetirizine in an HCT-60 coater using one spray nozzle and a spray rate of 40 g/minute. The final taste mask coating was then applied using a spray rate of 40 g/minute. The formulation did not form mono-alcohol esters of cetirizine, since no mono-alcohols reactive to cetirizine were used in the formulation. No significant esters of cetirizine were formed with other hydroxyl-containing excipients.

EXAMPLE 4

A pseudoephedrine tablet core of the composition given below was made by the following procedure. Approximately 56 kg of a wet granulation was prepared by first blending ingredients 1–5 in a 5 cubic foot blender for 20 minutes. It was then milled and reblended for another 15 minutes. Half of the blend was transferred to a 140 quart Hobart mixer. The 50/50 solution of isopropyl alcohol and ethanol (about 7.7 kg) was added slowly over 12 minutes such that the blend was thoroughly wetted and actually appeared to be "over-wet". The granulation was mixed for about 35 more minutes. The wet mass was tray dried in a forced air oven at 50° C. for 12–16 hours.

The dried granulation was milled at slow speed. The two portions of milled granulation were combined in a 5 cubic foot blender and blended for 5 minutes. Previously milled sodium chloride was added to the blender to account for 5.6% of the blend. It was blended for 5 more minutes. To this, 0.5% of magnesium stearate was added and blended an additional 5 minutes. The lubed granulation was compressed into tablet cores weighing approximately 600 mg using 7/16″ standard round concave tooling on a conventional rotary tablet press.

| TABLET CORE | | | |
|---|---|---|---|
| Component | Grade | % w/w of finished blend and tablet | Weight (mg/tablet) |
| 1. Pseudoephedrine HCl | USP | 40.00 | 240.00 |
| 2. Lactose, Anhydrous | NF | 15.37 | 92.20 |
| 3. Calcium Phosphate Dibasic, Anhydrous | USP | 24.93 | 149.60 |
| 4. Ethylcellulose, Standard 100 Premium | NF | 9.07 | 54.40 |
| 5. Povidone (Plasdone C-15) | USP | 4.53 | 27.20 |
| 6. Isopropyl Alcohol | USP | | (90.00)* |
| 7. Ethanol, 95% | USP | | (90.00)* |
| 8. Sodium Chloride | USP | 5.60 | 33.60 |
| 9. Magnesium Stearate | NF | 0.50 | 3.00 |
| Total | | 100.00 | 600.00 |

*() denotes a volatile component, not present in the final dosage form.

The membrane coating described in the table below was applied to the tablet cores in a perforated tablet coating pan (Hi-Coater, HCT-30, Vector Corp.). A tablet core batch of about 1200 grams was coated by spraying the membrane solution at about 30 g/min while maintaining an outlet temperature of about 24° C. After a 20% by weight membrane was applied, the tablets were dried for approximately 16–24 hours at 50° C. on trays in a forced air oven.

| MEMBRANE COATING | | | |
|---|---|---|---|
| Component | Grade | % w/w of coating solution | (mg/tablet) |
| 1. Pseudoephedrine HCl 240 mg Tablet Core | | | 600.00 |
| 2. Ethylcellulose, Standard 100 Premium | NF | 7.2 | 76.46 |
| 3. Cellulose Acetate | NF | 0.8 | 8.50 |
| 4. Polyethylene Glycol (Carbowax 3350) | NF | 3.3 | 35.04 |
| 5. Purified Water | USP | 3.3 | (35.47)* |
| 6. Isopropyl Alcohol | USP | 10.6 | (112.14)* |
| 7. Ethanol, 95% | USP | 22.0 | (233.63)* |
| 8. Acetone | NF | 52.8 | (560.71)* |
| Total | | 100.00 | 720.00 |

*() denotes a volatile component, not present in the final dosage form.

The dried tablets were then subsequently coated with the cetirizine HCl-containing coating shown in the following table. The drug layer was overcoated onto about 1100 grams of membrane coated tablets in a perforated tablet coating pan (Hi-Coater, HCT-30, Vector Corp.). The drug solution was sprayed at about 5 g/min while maintaining an outlet temperature of about 40° C. Enough drug layer was applied such that the tablet cores were overcoated with about 10 mg of cetirizine hydrochloride.

| CETIRIZINE/PSEUDOEPHEDRINE COATING | | | |
|---|---|---|---|
| Component | Grade | % w/w of coating soln | Weight (mg/tablet) |
| 1. Pseudoephedrine HCl 240 mg AM Coated Tablet | Pharm | | 720.00 |
| 2. Cetirizine HCl | Pharm | 1.7 | 10.00 |
| 3. Opadry, Clear (YS-5-19010) | Pharm | 5.8 | 35.00 |
| 4. Purified Water | USP | 92.5 | (555.00)* |
| Total | | 100.00 | 765.00 |

*() denotes a volatile component, not present in the final dosage form.

To these tablets a further taste masking layer was applied by spraying a 5% aqueous solution of Opadry, clear (YS-5-19010) increasing the individual tablet weight by about 23 mg. The solution was sprayed at about 5 g/min while maintaining an exhaust temperature of about 40° C.

| TASTE MASK COATING | | | |
|---|---|---|---|
| Component | Grade | % w/w of coating soln | Weight (mg/tablet) |
| 1. Cetirizine HCl/Pseudoephedrine HCl (10/240 mg) Tablet | Pharm | | 765.00 |
| 2. Opadry, Clear (YS-5-19010) | Pharm | 5.0 | 23.00 |
| 3. Purified Water | USP | 95.0 | (437.00)* |
| Total | | 100.00 | 788.00 |

*() denotes a volatile component, not present in the final dosage form.

These overcoated tablets were subjected to the following storage conditions as part of an accelerated stability study: 50° C., 40° C., 30° C. and 5° C. Degradation to the cetirizine ester of PEG3350 was determined after 12 weeks and 18 months as shown in the table below.

| Storage Conditions | % PEG 3350 ester of Cetirizine as determined relative to the cetirizine peak | |
|---|---|---|
| | 12 weeks | 18 months |
| 50° C. | 0.40 | |
| 40° C. | 0.17 | |
| 30° C. | 0.06 | 0.09 |
| 5° C. | ND | 0.01 |

ND = none detected

What is claimed is:

1. A solid dosage form comprising cetirizine and pseudoephedrine
    wherein an amount of at least about 75% of said pseudoephedrine is contained in a core comprising said amount, whereby release of said amount of pseudoephedrine into an environment of use is sustained;
    wherein said cetirizine is contained as an immediate-release component in said dosage form; and
    wherein said dosage form is substantially free of alcohols having a molecular weight lower than 100 and reactive derivatives thereof, said alcohol and/or derivatives being present in an amount less than that required to react with 5% of the cetirizine in the dosage form.

2. A dosage form as defined in claim 1, wherein said core is a matrix core comprising pseudoephedrine and a hydrophilic matrix polymer.

3. A dosage form as defined in claim 2, wherein said hydrophilic matrix polymer is selected from hydroxypropylmethyl cellulose (HPMC), hydroxypropyl cellulose (HPC), poly(ethylene oxide), poly(vinyl alcohol), xanthan gum, carbomer, carrageenan, and zooglan.

4. A dosage form as defined in claim 3, wherein said polymer is HPMC.

5. A dosage form as defined in claim 2, wherein said core comprises, by weight, about 50% to about 80% pseudoephedrine, about 15% to about 35% HPMC, 0% to about 35% lactose, 0% to about 15% PVP, 0 to 20% microcrystalline cellulose, and about 0.25% to about 2% magnesium stearate.

6. A dosage form as defined in claim 2, wherein said core is coated with an immediate release coating comprising cetirizine and a water soluble film forming polymer.

7. A dosage form as defined in claim 1, wherein said core comprises an immediate release pseudoephedrine composition surrounded by a rate limiting membrane.

8. A dosage form as defined in claim 7, wherein said membrane is a cellulose ester or cellulose ether.

9. A dosage form as defined in claim 7, in the form of a an osmotic delivery system.

10. A solid dosage form, in the form of a tablet, comprising cetirizine and pseudoephedrine wherein at least a portion of said pseudoephedrine is contained in a core comprising said portion, whereby release of said portion of pseudoephedrine into an environment of use is sustained over a period of 4 to 36 hours;

wherein said core comprises about 60 to 360 mg of pseudoephedrine, about about 70 to about 425 mg of compressible excipients, about 2 to about 17 mg binder, and about 0.5 to about 4 mg of lubricant;

wherein said cetirizine is contained as an immediate-release component in said dosage form; and wherein said dosage form is substantially free of alcohols having a molecular weight lower than 100 and reactive derivatives thereof, said alcohol and/or derivatives being present in an amount less than that required to react with 5% of the cetirizine in the dosage form.

11. A dosage form as defined in claim 10, wherein said portion of pseudoephedrine contained in said core is at least about 75%.

* * * * *